US011452589B2

(12) United States Patent
Kalfon

(10) Patent No.: US 11,452,589 B2
(45) Date of Patent: *Sep. 27, 2022

(54) IMPLANTABLE ANCHORING DEVICE AND METHODS OF USE

(71) Applicant: Allevetix Medical Ltd., Caesarea (IL)

(72) Inventor: Ziv Kalfon, Ein Hod (IL)

(73) Assignee: Allevetix Medical Ltd., Caesarea (IL)

( * ) Notice: Subject to any disclaimer, the term of this patent is extended or adjusted under 35 U.S.C. 154(b) by 379 days.

This patent is subject to a terminal disclaimer.

(21) Appl. No.: 16/699,451

(22) Filed: Nov. 29, 2019

(65) Prior Publication Data

US 2020/0100888 A1 Apr. 2, 2020

Related U.S. Application Data

(63) Continuation-in-part of application No. 16/223,170, filed on Dec. 18, 2018, now Pat. No. 10,631,971, which is a continuation of application No. 15/954,757, filed on Apr. 17, 2018, now Pat. No. 10,368,976.

(60) Provisional application No. 62/613,065, filed on Jan. 3, 2018.

(51) Int. Cl.
*A61F 2/04* (2013.01)
*A61F 5/00* (2006.01)
*A61L 31/02* (2006.01)
*A61L 31/10* (2006.01)

(52) U.S. Cl.
CPC .............. *A61F 2/04* (2013.01); *A61F 5/0036* (2013.01); *A61F 5/0076* (2013.01); *A61L 31/022* (2013.01); *A61L 31/10* (2013.01); *A61F 2002/045* (2013.01); *A61F 2220/0008* (2013.01); *A61F 2220/0033* (2013.01); *A61F 2230/0065* (2013.01); *A61F 2240/001* (2013.01)

(58) Field of Classification Search
CPC ..... A61B 2017/00588; A61F 2002/045; A61F 5/0036; A61F 5/0073
See application file for complete search history.

(56) References Cited

U.S. PATENT DOCUMENTS

| | | | |
|---|---|---|---|
| 5,059,193 A * | 10/1991 | Kuslich | ................. A61F 2/4455 606/279 |
| 8,529,628 B2 * | 9/2013 | Marino | .............. A61B 17/8858 623/17.11 |
| 9,636,245 B2 | 5/2017 | Chamorrro, III et al. | |
| 10,368,976 B2 | 8/2019 | Kalfon | |
| 10,631,971 B2 | 4/2020 | Kalfon | |
| 2002/0055757 A1 * | 5/2002 | Torre | ...................... A61F 5/003 606/192 |
| 2008/0058840 A1 | 3/2008 | Mbrecht et al. | |
| 2008/0177395 A1 | 7/2008 | Stinnette | |
| 2012/0095484 A1 | 4/2012 | Dominguez | |

(Continued)

*Primary Examiner* — Megan Y Wolf
(74) *Attorney, Agent, or Firm* — Katterle Nupp LLC; Paul Katterle; Robert Nupp

(57) ABSTRACT

A method of using an implantable device provides an implantable device including a plurality of arcs. Each arc contains a multiplicity of links. The implantable device further includes a device closure pin, a lock-in unit attached and located between the three arcs, and a quick-release unit attached and located between three arcs. The plurality of arcs, the lock-in unit, and the release unit form a closed contour. The closed contour of the implantable device, in a rigid state is a three-dimensional shape.

18 Claims, 11 Drawing Sheets

(56) References Cited

U.S. PATENT DOCUMENTS

| | | |
|---|---|---|
| 2012/0095497 A1 | 4/2012 | Babkes et al. |
| 2013/0131822 A1* | 5/2013 | Lewis ................ A61B 17/7266 623/21.19 |
| 2014/0012383 A1 | 1/2014 | Triplett et al. |
| 2016/0074174 A1 | 3/2016 | Halverson et al. |
| 2017/0027621 A1 | 2/2017 | Shenoy et al. |
| 2019/0008654 A1 | 1/2019 | Thommen et al. |

* cited by examiner

SECTION N-N

IMPLANTABLE ANCHORING DEVICE AND METHODS OF USE

CROSS-REFERENCE TO RELATED APPLICATION(S)

The present application is a continuation-in-part of U.S. patent application Ser. No. 16/223,170, which is a continuation of U.S. patent application Ser. No. 15/954,757 filed on Apr. 17, 2018, now U.S. Pat. No. 10,368,976, which claims the benefit of U.S. Provisional Patent Application 62/613,065 to Kalfon, Ziv filed on Jan. 3, 2018, all of which are incorporated herein by reference.

TECHNICAL FIELD

The present disclosure generally relates to a device that is inserted into a body cavity using intraoral procedures and positioned within a body cavity by a deformation of the shape and rigidity of the device.

BACKGROUND

Several medical procedures require placement of a medical device in the lumen of a human or animal body and in particular, in the stomach. Once inserted, the movement of the inserted medical device has to be constrained, and this is achieved by the use of anchors. U.S. Pat. No. 9,636,245 to Chamorro describes a gastrointestinal device including a proximal element configured to reside in the stomach and a distal element configured to reside in an intestine, where the proximal element is configured to resist migration over time. US Pat. Application No. 2008/0058840 to Albrecht describes an alternative proximal element for placement within a hollow body organ. The proximal element includes a member having a first shape for delivery to the hollow body and a second shape for implantation therein. The member has sufficient rigidity in its second shape to exert an outward force against an interior of the hollow body to bring together two substantially opposing surfaces of the hollow body. US Pat. Application No. 2012/0095385 to Domingues describes a gastric balloon that is introduced in the stomach. The balloon occupies space in the stomach, thereby leaving less room for food and creating a feeling of satiety for the patient. U.S. Pat. No. 6,994,715 to Gannoe discloses expandable and space-occupying devices that are inserted into the stomach of a patient and may be maintained within the stomach by anchoring or otherwise fixing the device to the stomach wall. Patent Cooperation Treaty Publication No. 2007/076021 to Haller describes a gastrointestinal device, which is a bag stuffed with digestive resistant or indigestible material. The bag is located in the gastric lumen in a compacted configuration. The bag is then manipulated into, or allowed to assume, a second expanded configuration sufficiently large to maintain the bag within the stomach and not to be passed through the pylorus and into the intestines. The examples of implants described in the listed above patents suffer from certain drawbacks when inserted within a lumen of the human body and do not provide the long term required implantation stability.

SUMMARY

This current disclosure describes an implantable device including at least three (plurality) of arcs with each arc including a multiplicity of links. The implantable device is configured to be in either of two states; a flexible state in at least one plane of the device or a rigid state in all other planes of the device. In the rigid state, the device has a three-dimensional curved shape. The implantable device includes at least but not limited to: device closure pin; a lock-in unit; a quick-release unit; a plurality of arcs where each arc includes a multiplicity of links connected to two other links or a link on one side and either a lock-in unit or release unit on an opposing side. The implantable device is inserted into a body cavity using intraoral procedures. During insertion, the device closure pin is attached only at one side and in one example to the quick release unit, and the implantable device is in the flexible state. The flexibility of the implantable device affords the device the ability to follow the contours of the body orifice and facilitates the insertion of the device with minimal patient discomfort. The implantable device is releasably connected to the intraoral insertion equipment at the lock-in unit. After insertion of the implantable device into the human body and placement of the implantable device in the target body cavity, the device closure pin is pulled into the lock-in unit and locked into place. The device closure pin is now attached at both ends of the pin and transforms the implantable device into a rigid state. In the rigid state, the implantable device has a three-dimensional curved shape such as a sphere or an ellipsoid providing anchoring features and preventing mobility of the implantable device in the body cavity.

In one example, a functional unit providing a body-related function is attached to the release unit. An example of a functional unit is an intragastric sleeve adapted to reduce the intake of food items in the intestine.

DETAILED DESCRIPTION OF ILLUSTRATIVE EMBODIMENTS

Figure 1A:
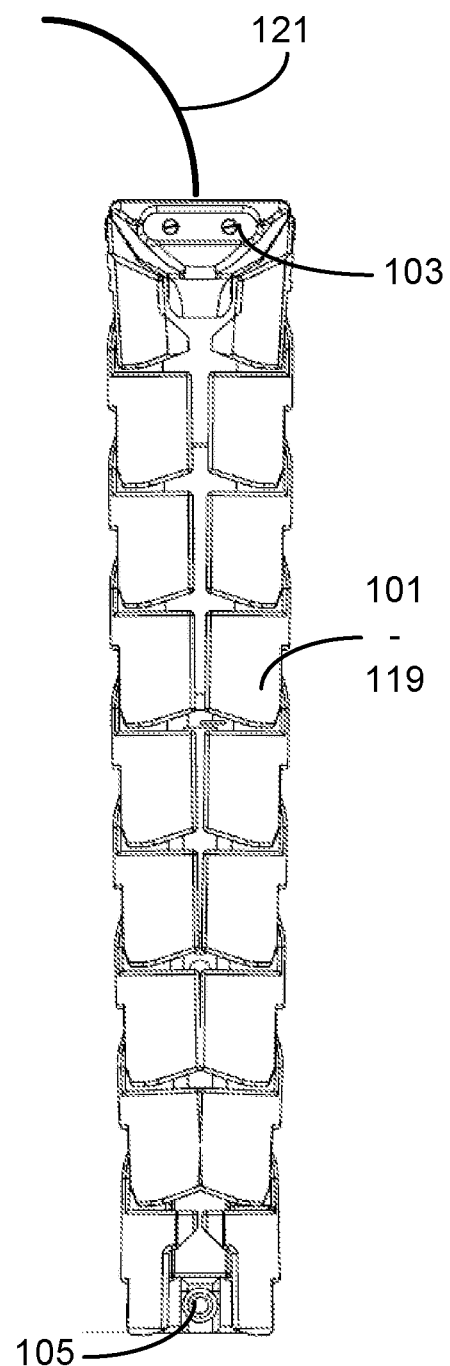
FIG. 1A is an example of an implantable device consisting of two arcs and multiple links and configured to be flexible in at least one plane.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure. This disclosure is drawn, among other things, to a device that is inserted into a human or animal body using intraoral procedures and positioned within a body cavity by a change of the shape and rigidity of the device.

In examples/patents of the implantable devices described above, the proximal element is in contact with the pylorus. The proximal element has a rounded shape, and as a result, it exerts an expansion force on the pylorus which extends the pylorus opening over time and dislodges the proximal element. Such implants suffer from migration within a lumen of a human or animal body and do not provide the long term required implantation stability. It is desirable to have a proximal element which does have a three-dimensional curved shape that could be in contact with walls of the stomach, the shape large enough and does not slide into the pylorus and provides the long term required implantation stability.

FIG. 1A is an example of an implantable device consisting of two arcs and multiple links and configured to be flexible in at least one plane. The implantable device includes at least but not limited to; a lock-in unit 103; a quick-release unit 105 a multiplicity of links 101, 113, 115, 117, 119 (collectively 101-119 or 101) where each link 101 is connected to two other links 101 or to a link 101, 113, 115, 117, 119 on one side and either a lock-in unit 103 or a release unit 105 on an opposing side. The implantable device is inserted into a body cavity using intraoral procedures. During insertion, the flexibility of the implantable device affords the device the ability to follow the contours of the body orifice and facilitates insertion with minimal discomfort to the patient. The implantable device connects to delivery or insertion equipment at lock-in unit 103. In one example, a functional unit providing a body-related function is attached to a quick-release unit 105. An example of a functional unit is an intragastric sleeve adapted to reduce the intake of food items in the intestine.

Figure 1B:
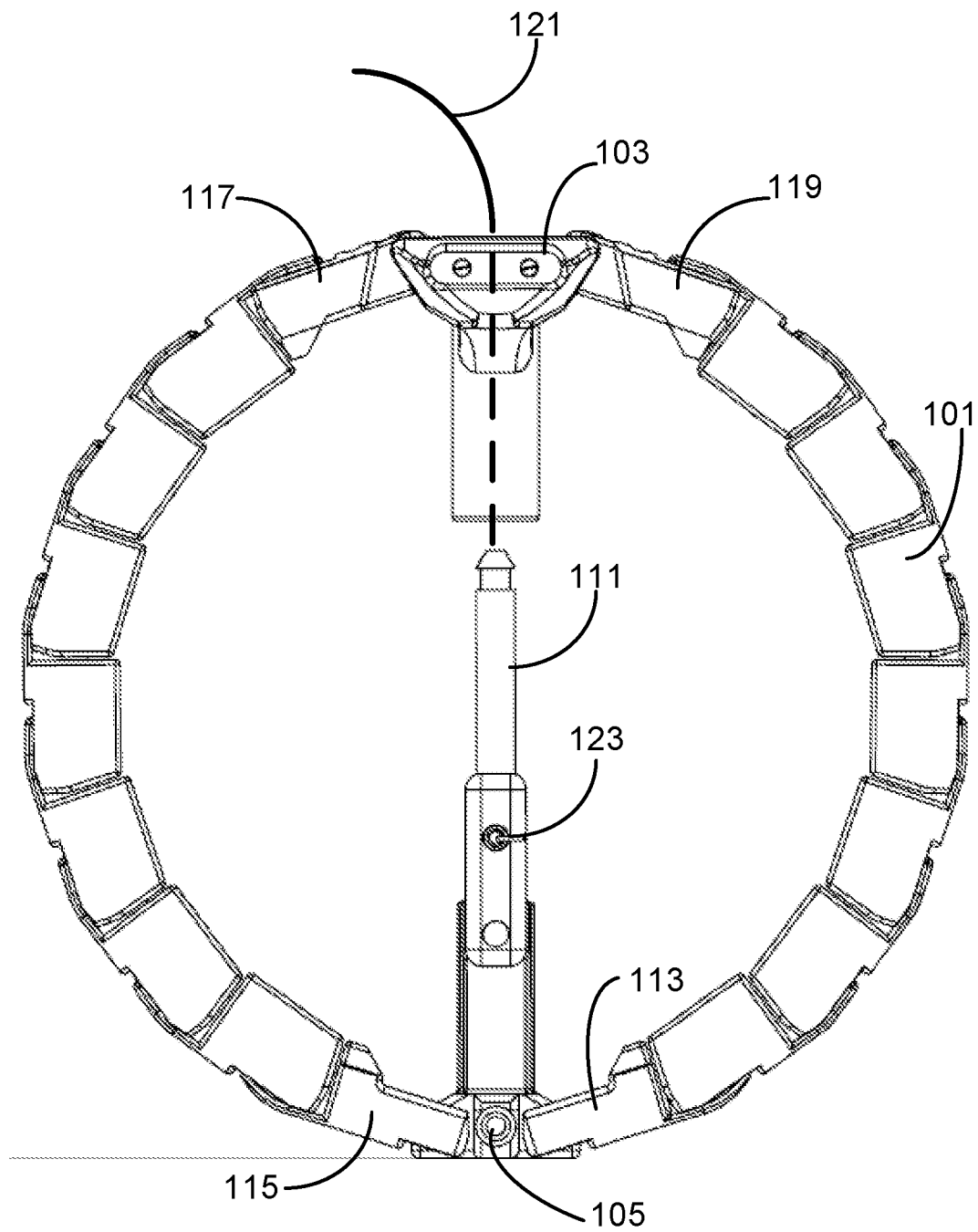
FIG. 1B is an example of an implantable device consisting of two arcs and multiple links just before being configured to be rigid in all planes.

FIG. 1B is an example of an implantable device including two arcs and multiple links just before being configured to be rigid in all planes. The implantable device is transformed from a flexible state as described in FIG. 1A to a rigid state as described in FIG. 1C by pulling a cord 121 attached to a device closure pin 111 (FIG. 1B) and passing through lock-in unit 103. Device closure pin 111 follows the cord 121 into lock-in unit 103, where a locking mechanism holds the device closure pin 111 in place. The locked-in device closure pin 111 exerts a force on the implantable device links 101-119, constricting the relative movement of the links and transitioning the implantable device to a rigid state. The transition of the implantable device from a rigid state to a flexible state facilitates removal of the implantable device from the body cavity. Removal of release pin 123 from device closure pin 111, releases the device closure pin 111 from the release unit 105 and transitions or transforms the implantable device to a flexible state. After transitioning the implantable device to a flexible state, it is removed from the body cavity with intraoral procedures. Examples of materials for manufacturing the links 101 include but are not limited to: Titanium; Stainless steel; Cobalt, Chrome, Nitinol alloy, thermoset plastics and similar materials or composition of said materials.

Additionally, a Teflon™ (polytetrafluoroethylene) coating or overcoat enhances the atraumatic properties of the links 101-119 surfaces. (The surfaces are considered "atraumatic" because they do not cause trauma to the body.) Examples of materials for the device closure pin 111 and the release pin 123 include but are not limited to; Stainless steel; Titanium; Cobalt, Chrome, Nitinol alloy, thermoset plastics and similar materials or composition of said materials. In one example, links 101 of the implantable device are manufactured using additive manufacturing processes, for example, 3D printing. Links 101, lock-in unit 103, quick-release unit 105 and interconnecting pins are manufactured concurrently and in a connected manner so that at the additive manufacturing cycle results in a connected closed contour of links 101-119, lock-in unit 103 and quick release unit 105.

Hence, described in one example is an implantable device including a multiplicity of links 101-119; a device closure pin 111; a lock-in unit 103 attached and located between two links 117, 119; a release unit 105 attached and located between two links 113, 115. The multiplicity of links 101-119, lock-in unit 103 and release unit 105 construct a closed contour; and wherein the implantable device is in a flexible state when the device closure pin 111 is coupled to the lock-in unit 103 or the quick-release unit 105 and rigid state when the device closure pin 111 is attached to both the lock-in unit 103 and quick-release unit 105.

Figure 1C:
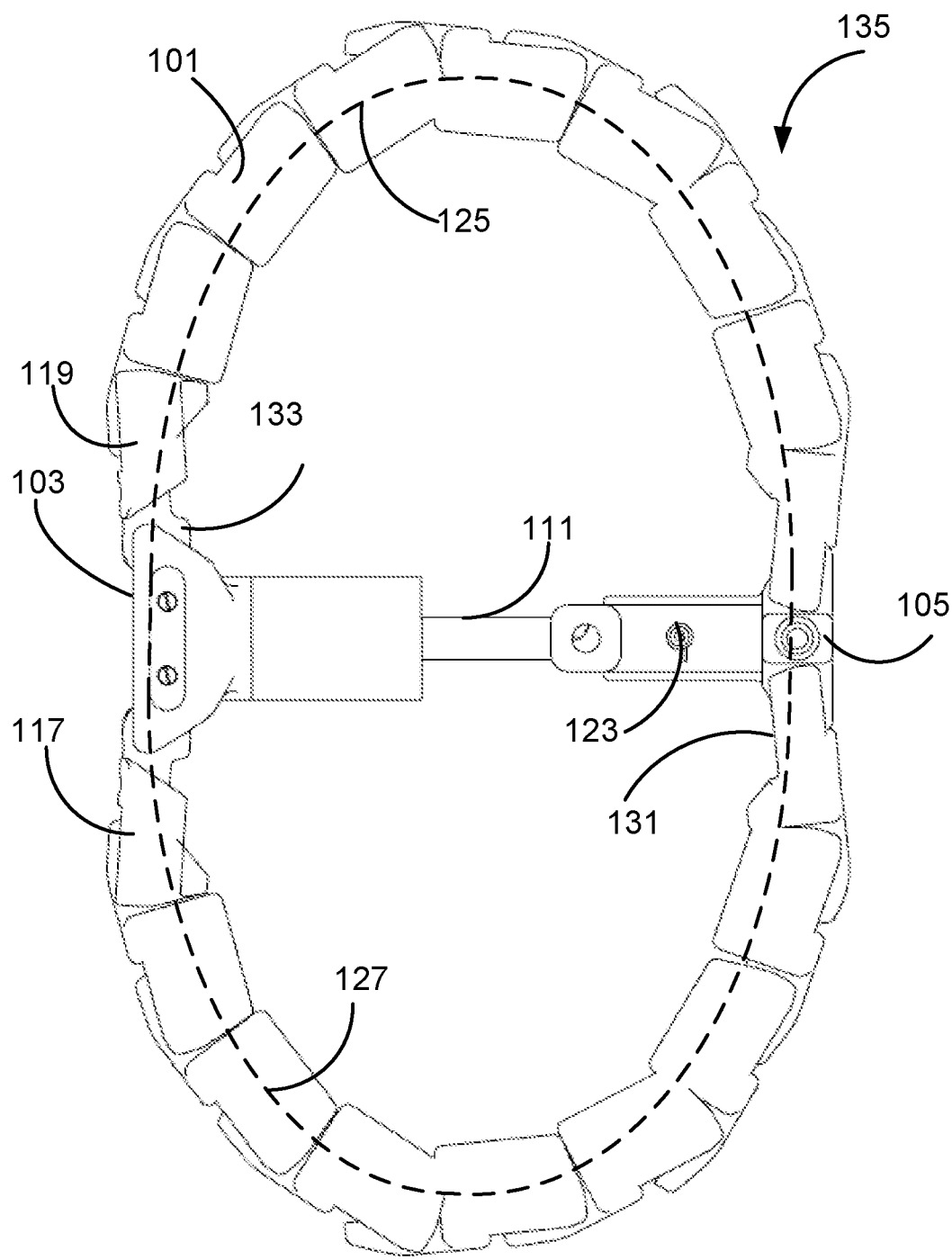
FIG. 1C is an example of an implantable device consisting of two arcs and multiple links and configured to be rigid in all planes.

FIG. 1C is an example of a side view of the implantable device in the rigid state 135, where the closed contour and device closure pin 111 form a figure eight. In an alternative example an implantable device comprising; a plurality of links 101-119 constructing a closed loop wherein a link 101, 113, 115, 117 is connected to two other links 101-119; a device closure pin 111; wherein the implantable device is flexible when only one side of device closure pin 111 is attached to a link 101-119 and rigid when both sides of the device closure pin 111 is attached to a link 101-119. In a further example the closed contour of an implantable device in a rigid state 135 is oval and is configured to follow the shape of two arcs 125, 127 and two interconnecting sections 131, 133 where the absolute radius of the two arcs sections 125, 127 is at least 5 times larger the absolute radius of the interconnecting sections 131, 133. The radius of each of the arcs sections 125, 127 is of opposite sign. In a further example, the closed contour of an implantable device in a rigid state is oval and comprised of two arcs 125, 127 and two interconnecting sections 131, 133 where the two interconnecting sections 131, 133 are substantially straight. In a further example, the closed contour of an implantable device in a rigid state has a shape of figure eight comprised of two arcs and two connected interconnecting sections. The resulting shape of the implantable device in a rigid state which is in contact with the pylorus is substantially straight and hence does not exert an expanding force on the pylorus, ensuring the long term stability of the implanted device.

Figure 1D:
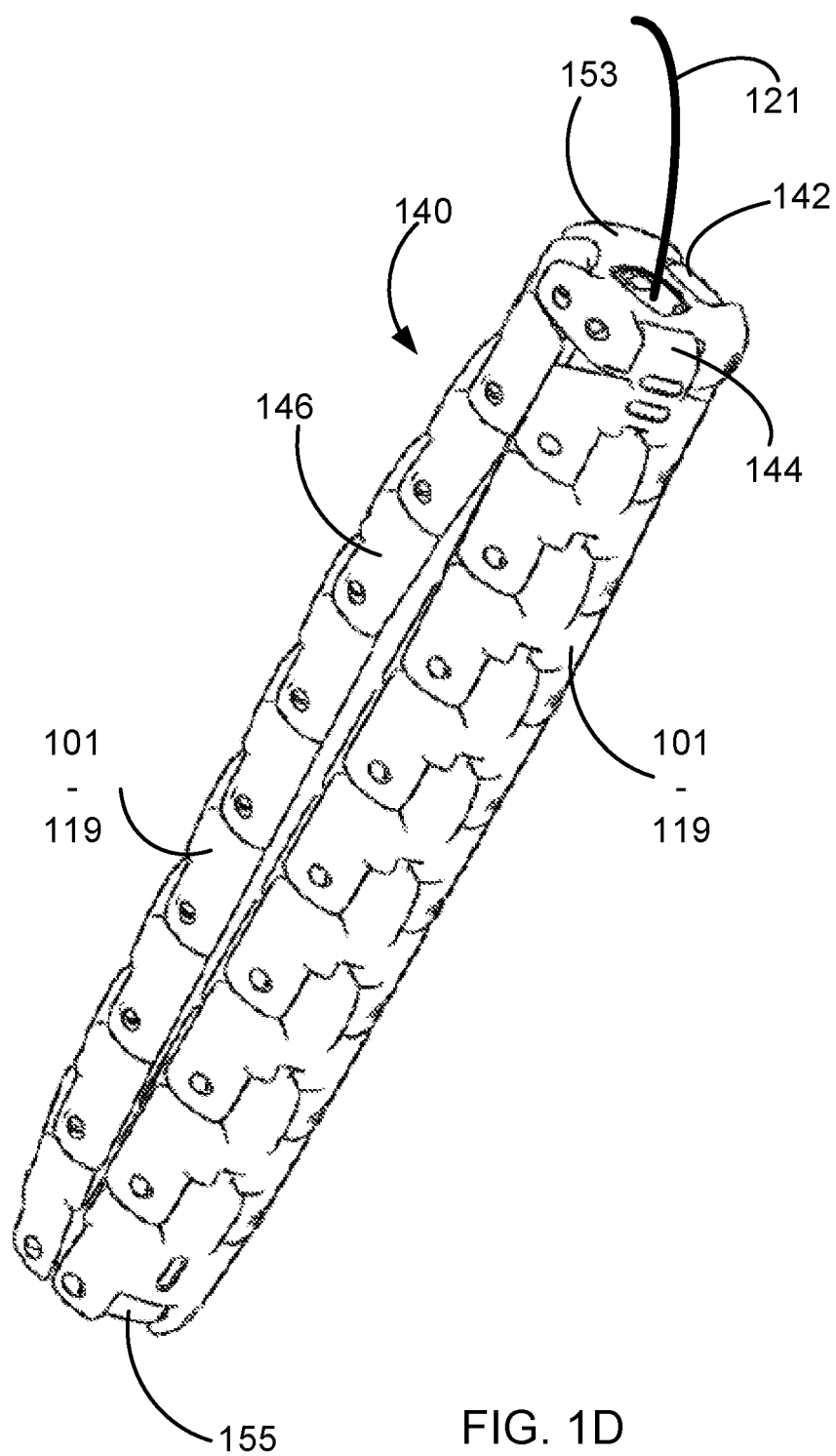
FIG. 1D is an example of an implantable device consisting of three arcs and multiple links.

FIG. 1D is an example of an implantable device consisting of three arcs and multiple links. FIG. 1D illustrates implantable device 140 in a first or flexible state. Implantable device 140 consists of three arcs 142, 144, and 146, and each arc includes multiple links 101-119. Arcs 142, 144, and 146 with multiple links 101-119 are configured to be sufficiently flexible for an intraoral introduction into a recipient body. The implantable device 140 includes at least but not limited to; a lock-in unit 148; a quick-release unit 155; a multiplicity of links 101-119. Each link 101-119 connects to two other links 101-119 or a link 101-119 on one side and either a lock-in unit 153 or a quick-release unit 155 on an opposing side. The implantable device 140 in a first or flexible state is inserted into a body cavity using intraoral procedures. During insertion, the flexibility of the implantable device affords the implantable device 140 the ability to follow the contours of the body orifice and facilitates insertion with minimal discomfort to the patient. The implantable device 140 is connected to delivery or insertion equipment at lock-in unit 153. In one example, a functional unit providing a body-related function is attached to a quick-release unit 155. An example of a functional unit is an intragastric sleeve adapted to reduce the intake of food items in the intestine.

Figure 1E:
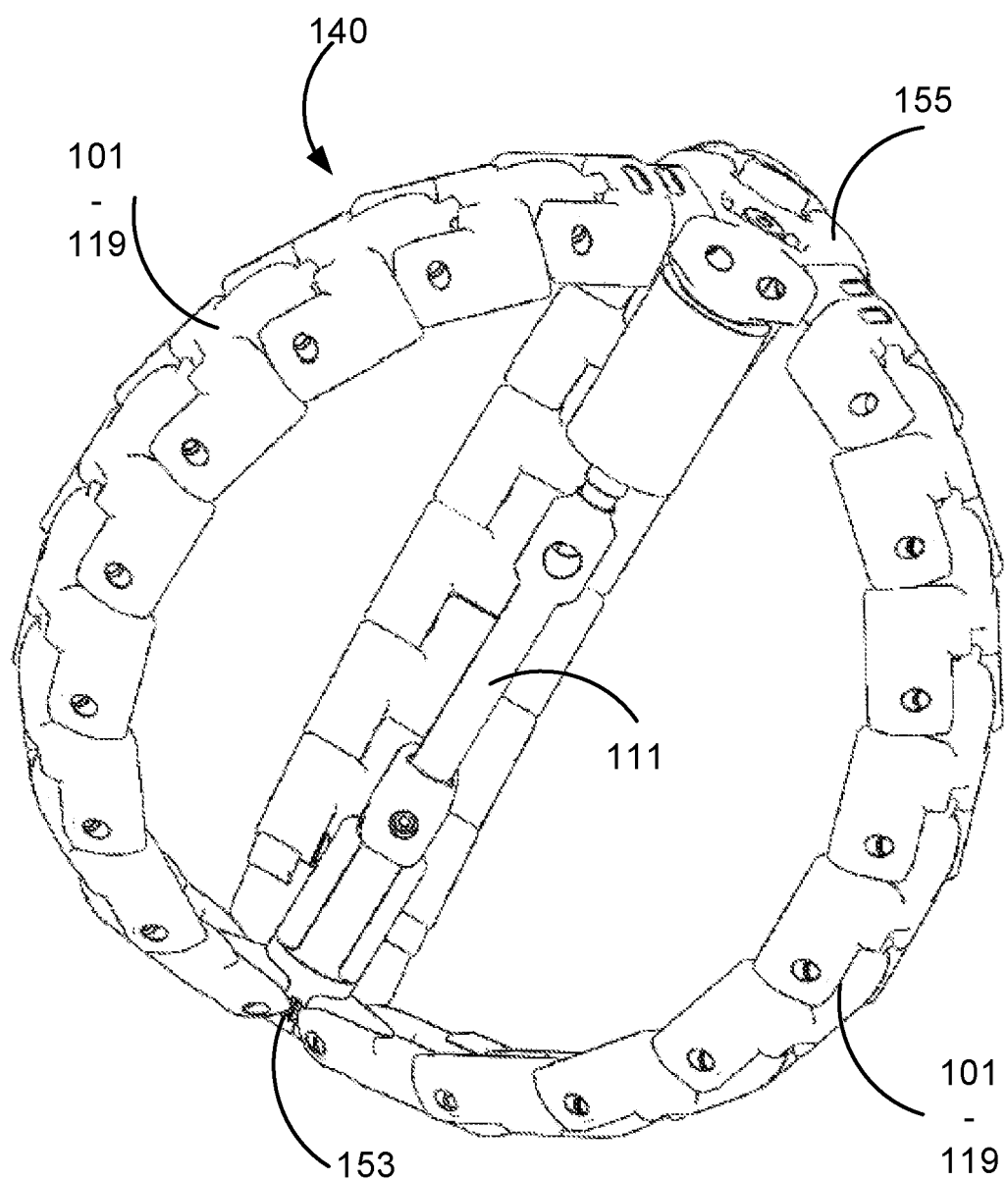
FIG. 1E is an example of an implantable device consisting of three arcs and multiple links and shown in a rigid state.

FIG. 1E is an example of an implantable device consisting of three arcs and multiple links and shown in a rigid state. The implantable device 140 in the first configuration is in a flexible state. In the second configuration or rigid state, implantable device 140 forms a closed contour wherein the three arcs 142, 144, and 146, lock-in unit 153, and quick-release unit 155 construct a closed three-dimensional curved shape device. The closed three-dimensional curved shape of implantable device 140 could be one of a group of shapes consisting of a sphere or an ellipsoid.

All links (101-119) surfaces are atraumatic surfaces made of Titanium. Additionally, a Teflon™ (polytetrafluoroethylene) coating or overcoat enhances the atraumatic properties of the links 101-119 surfaces. Usually, the links (101, 113, 115, 117, 119) are fabricated using additive manufacturing processes.

Figure 2A:
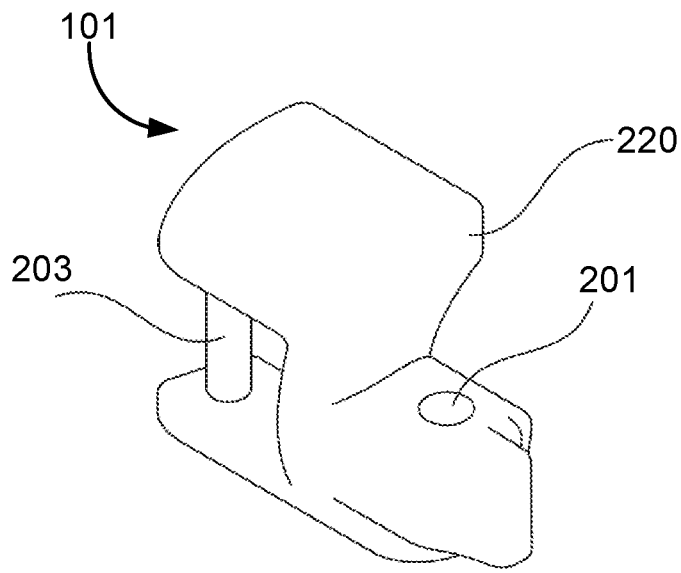
FIG. 2A is an example of a link of the implantable device.
Figure 2B:
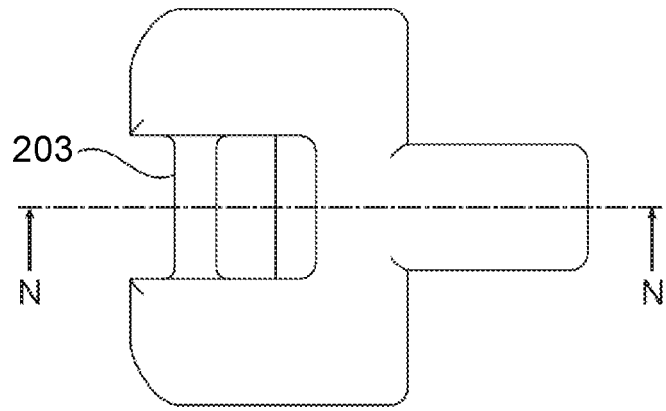
FIG. 2B is an example of a top view of a link of the implantable device.
Figure 2C:
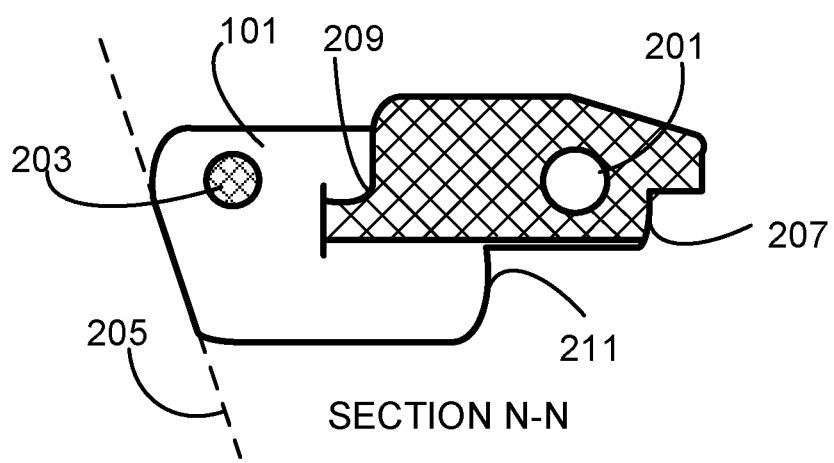
FIG. 2C is an example of a side view cross-section of a link of the implantable device at cut line NN from FIG. 2B.

FIG. 2A is an example of an implantable device link (FIG. 1A numerals 101-119.) A link 101-119 includes an attachment axis 203 and a pin cavity 201. The attachment axis 203 is configured to connect to a pin cavity 201 in a second link creating a closed contour composed of a multiplicity of links 101-119 where each link 101-119 is connected to two other links 101-119 or to a link 101 on one side and either a lock-in unit (FIG. 1B reference numeral 103 and FIG. 1E reference numeral 153) or release unit (FIG. 1B reference numeral 105 and FIG. 1E reference numeral 155) on an opposing side. FIG. 2B is an example of a top view of a link 101 of the implantable device. FIG. 2C is an example of a side view cross-section of a link of the implantable device at cut line N-N from FIG. 2B. Link 101 includes an attachment axis 203 and a pin cavity 201. The link further includes an inclined side 205. In the flexible state of the implantable device, one link 101 connects to a second link 101, where the axis 203 of one link 101 is inserted in the pin cavity 201 of a second link 101. The links 101 are free to move around the axle defined by their axis 203. The relative movement of the links 101 around the axle provides the required flexibility along one plane of an implantable device in the flexible state. In the constrained state inclined side 205 of one link 101 is pressed against the opposing side 211 of adjacent connecting link 101. The shape of the contour of the implantable device in the constrained state is determined by the relative angle of the inclined side 205 of one link 101, and the opposing side 211 of the adjacent link 101, which is in contact with said inclined side 205. In a further example, the aforementioned relative angle varies from link to link to configure a specific size shape of the closed contour of the implantable device in the rigid state.

Support recess 207 or 209 come into contact with support recess 209 or 207 of an adjacent link at a maximum preset angle and provide a constraint on the relative motion of the link 101 in the flexible state. The links comprise at least a base 220 (FIG. 2A); one or more connecting pins 203 and one or more vias 201. All links (FIG. 1A 101-119 and FIG. 2A 101) comprising the implantable device and pins 203 and pinholes 205 are manufactured concurrently so that a pin 203 of one link 101 is situated in a pinhole 205 of an adjacent link 101 or lock-in unit (FIG. 1A 103 and FIG. 1E 153) or quick release unit (FIG. 1A 105 and FIG. 1E 155) and providing a closed contour of links 101, lock-in unit (FIG. 1A 103 and FIG. 1E 153) and quick release unit (FIG. 1A 105 and FIG. 1E 155) at the end of the additive manufacturing cycle.

As illustrated in the example, the links consist of at least a base 220; one or more connecting axis 203 and one or more holes 201. Base 220 and a connecting axis 203 of one link (FIG. 1B-1E 101-119) which is located in a pinhole 201 of a second link (FIG. 1B-1E. 101-119) are fabricated concurrently using additive manufacturing processes.

Figure 3A:
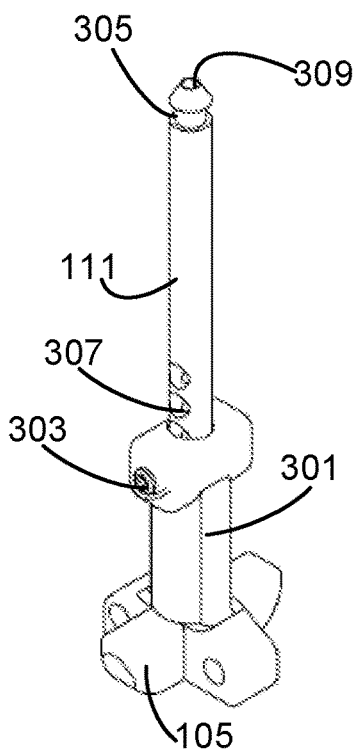
FIG. 3A is an example of device closure pin attached to a release unit.
Figure 3B:
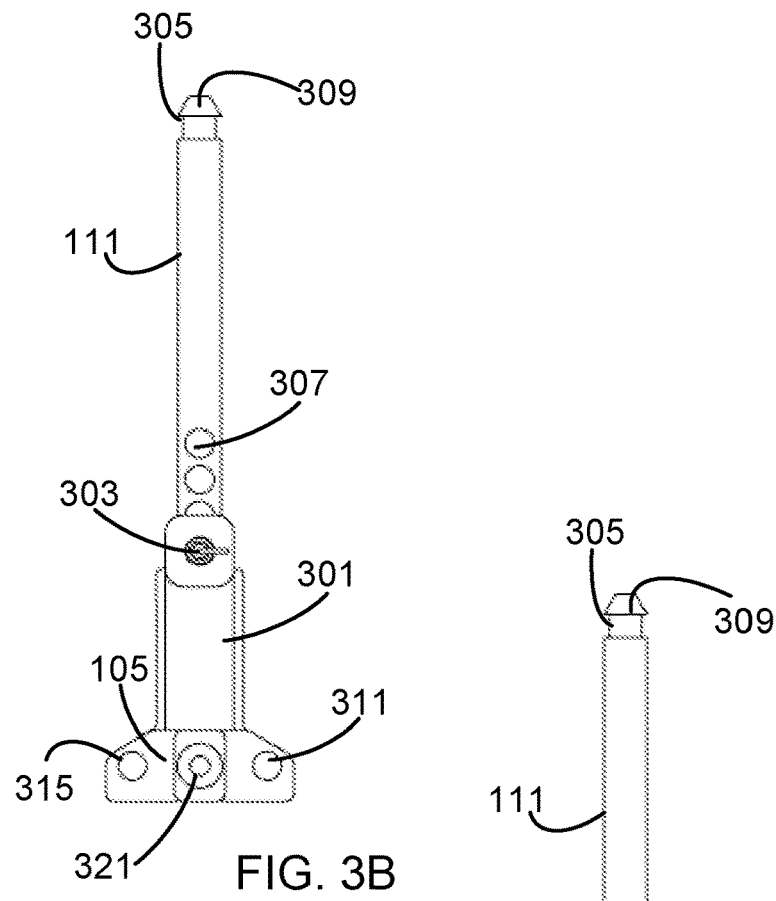
FIG. 3B is an example of a side view of a device closure pin attached to a release unit.
Figure 3C:
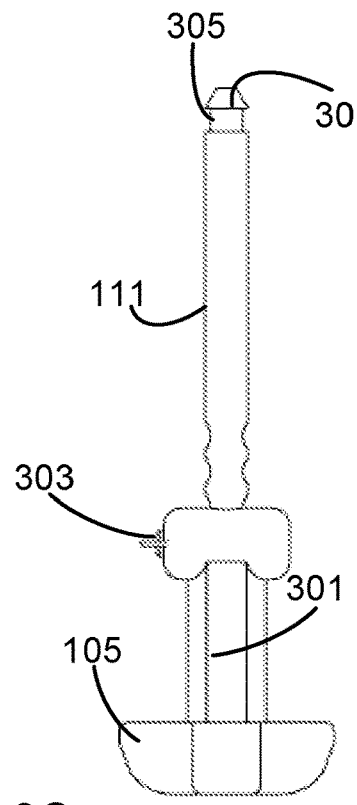
FIG. 3C is an example of a back view of a device closure pin attached to a release unit.

FIG. 3A is an example of a device closure pin 111 attached to a release unit 105 (or 155). The top side of device closure pin 111 is configured as a snap-in segment. The snap-in segment includes a recess 305 and a conical tip 309. In a further example, when the implantable device is in a flexible state, a cord (FIG. 1B—121) is connected to the top part of the conical tip 309. Pulling the cord (FIG. 1B—121) pulls the device closure pin 111 into a receptacle (FIG. 4—401) where it is locked in place due to the recess 305. The device closure pin 111 further includes one or more quick-release pinholes 307. FIG. 3B is an example of a side view of a device closure pin attached to a release unit. The device closure pin 111 further includes an attachment pin 315 and attachment pin cavity 311, which correspond to a link's (FIG. 2A—101) attachment pin (FIG. 2C—203) and attachment pin cavity (FIG. 2C—201). The pins are used to attach links on either side of the device closure unit. The device closure unit 105/155 further includes a quick release housing 301 and second pinhole 303. A device attachment pin is inserted into the quick release housing 301 and held in place by insertion of a quick release pin (FIG. 1B—123) through the second pinhole 303 and quick release pinhole 307 in the device closure pin 111. Before insertion in the body, the device closure pin 111 is attached to the quick-release unit 105/155. The effective length of the device closure pin 111 is adjusted by a choice through which quick-release pinhole 307 the quick-release pin (FIG. 1B—123) will pass through and lock the device pin 111 in place. The effective length of the device closure pin 111 determines the contour shape when the implantable device is in the rigid state. In a further example, the contour shape is configured to be essentially flat for at least one link on either side of the quick release unit 105. Sleeve connection pin 321 is the anchor point for a cord connecting the implantable device to an intestine sleeve. FIG. 3C is an example of a back view of a device closure pin attached to a release unit.

Figure 4A:
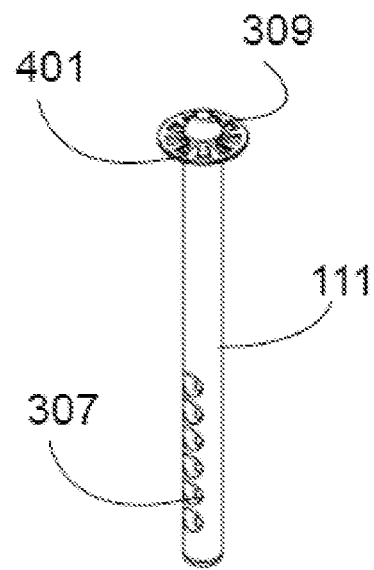
FIG. 4A is an example of device closure pin attached to a receptacle.
Figure 4B:
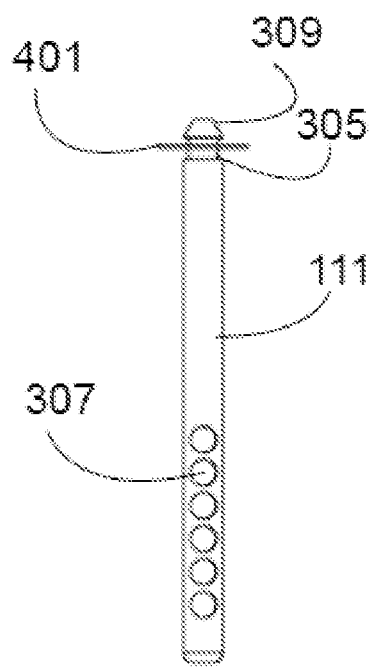
FIG. 4B is an example of a side view of a device closure pin attached to a receptacle.
Figure 4C:
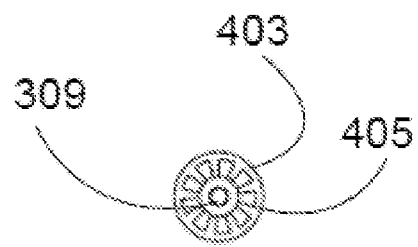
FIG. 4C is an example of a top view of a device closure pin attached to a receptacle.

FIG. 4A is an example of device closure pin 111 attached to a receptacle 401. FIG. 4B is an example of a side view of a device closure pin 111 attached to a receptacle 401 and FIG. 4C is an example of a top view of a device closure pin attached to a receptacle 401. In one example a receptacle 401 includes an outer ring 403 a plurality of spokes 405 which terminate short of the center of the receptacle 401 and enable the conical tip 309 of the device closure pin 111 to traverse the receptacle 401 and then lock the device closure pin 111 in place by extending into the device closure pin recess 305. Examples of materials for manufacturing the receptacle include but are not limited to; stainless steel Titanium; Stainless steel; Cobalt, Chrome, Nitinol alloy, thermoset plastics, and similar materials; or composition of said materials.

Closure pin 111 includes a conical tip 309 configured for insertion and lock-in into a receptacle 401 with an outer ring 403 and one or more spokes 405 and in, a further example the receptacle 401 is structured as slotted spring washer and configured to receive and hold a snap-in segment of device closure pin 111.

Figure 5A:
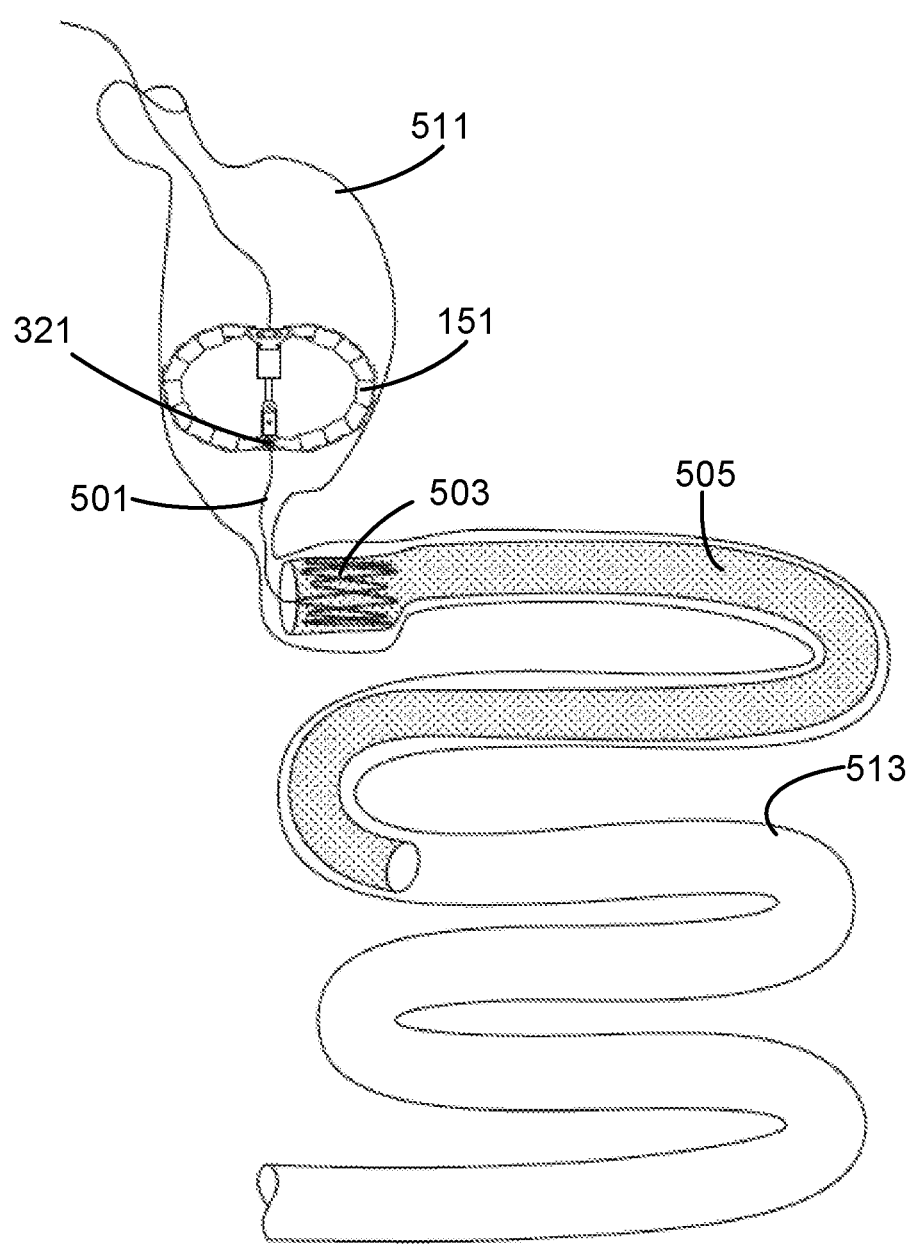
FIG. 5A is an example of a method of use of the implantable device consisting of two arcs and multiple links in the rigid state to constrain movement of the device in a body cavity.

FIG. 5A is an example of a method of use of an implantable device in the rigid state 135 to constrain implantable device movement in a body cavity. In one example, the implantable device in the rigid state 135 is fixed in the stomach 511. An intestine sleeve 505 is attached with the sleeve cord 501 to the implantable device in the rigid state 151 and inserted into the intestine 513. In a further example, the intestine sleeve 505 includes a wave anchor 503, which positions the intestine sleeve in place.

Figure 5B:
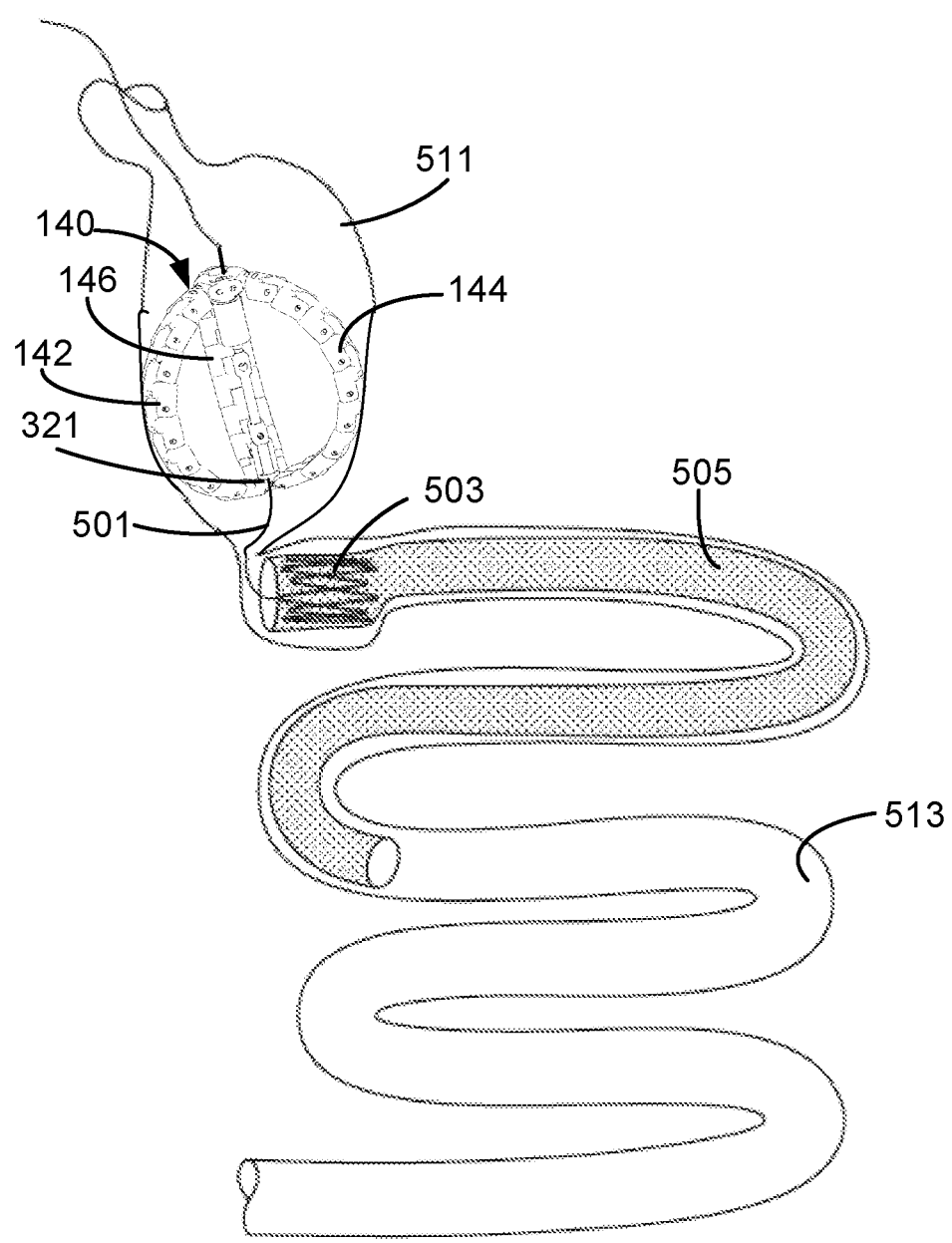
FIG. 5B is an example of a method of use of the implantable device consisting of three arcs and multiple links in the rigid state to constrain movement of the device in a body cavity.

FIG. 5B is an example of a method of use of the implantable device consisting of three arcs and multiple links in the rigid state to constrain movement of the implantable device in a body cavity. In the rigid state, the shape of implantable device 140 has a closed three-dimensional curved shape contour. Three arcs 142, 144, and 146 of device 140 open and anchor device 140 within stomach 511. Arcs 142, 144, and 146 of device 140 could be in contact with walls of stomach 511. The three-dimensional curved shape contour of unit 140 supports almost constant location of unit 140 within the stomach.

Figure 6A:
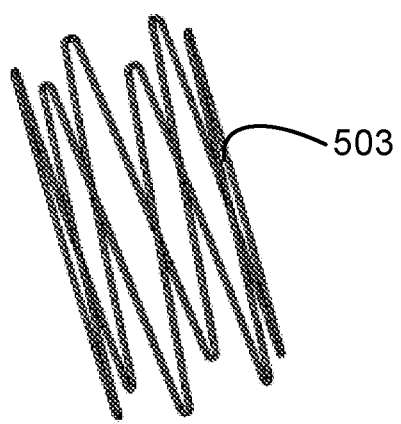
FIG. 6A is an example of a wave anchor in a folded configuration.
Figure 6B:
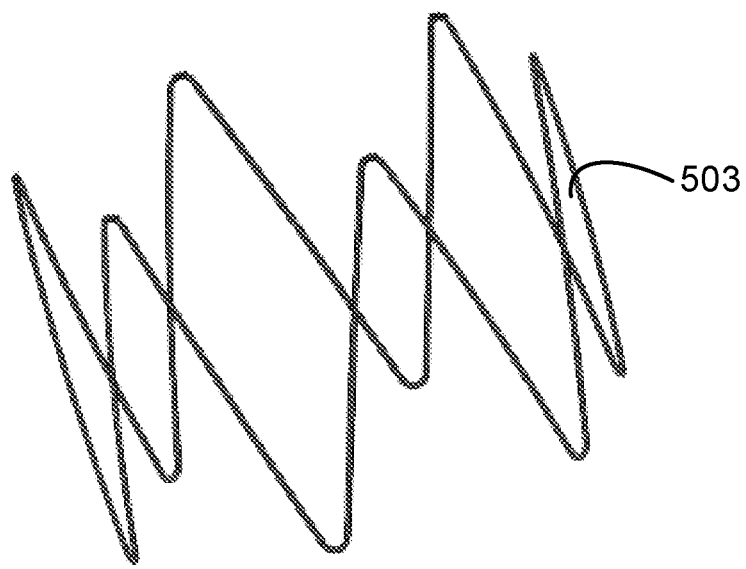
FIG. 6B is an example of a wave anchor in an extended configuration.

FIG. 6A is an example of the wave anchor 503 in a folded configuration and FIG. 6B is an example of the wave anchor in an expanded configuration.

Several examples have been described. Nevertheless, it will be understood that various modifications may be made without departing from the spirit and scope of the method. Accordingly, other examples are within the scope of the following claims:

What is claimed is:

1. An implantable device comprising:
   at least three arcs;
   a device closure pin;
   a lock-in unit attached and located at one end of the at least three arcs;
   a quick-release unit attached and located at an opposite end of the at least three arcs; and
   wherein the implantable device is transformable between a first flexible state and a second rigid state, wherein when the device closure pin is coupled to one of the lock-in unit and the quick-release unit, the implantable device is in the first flexible state and when the device closure pin is attached to both the lock-in unit and the quick-release unit, the implantable device is in the second rigid state, and wherein each of the at least three arcs includes links with atraumatic surfaces, wherein the links are connected together by pins such that the links are movable about the pins when the implantable device is in the first flexible state.

2. The implantable device of claim 1, wherein when the implantable device is in the second rigid state, the at least three arcs, the lock-in unit and the quick-release unit form a closed three-dimensional curved shape.

3. The implantable device of claim 2, wherein the closed three-dimensional curved shape is one of a group of shapes consisting of a sphere or an ellipsoid.

4. The implantable device of claim 1, wherein surfaces of the links are atraumatic surfaces comprised of titanium and wherein the atraumatic surfaces of the links further include a polytetrafluoroethylene coating or overcoat.

5. The implantable device of claim 4, wherein each of the links comprise at least a base, an attachment axis and one or more pinholes; and wherein the links are fabricated using additive manufacturing processes.

6. The implantable device of claim 5, wherein the base and the attachment axis of a first one of the links are fabricated concurrently using additive manufacturing processes, and wherein the attachment axis of the first one of the links is located in a pinhole of a second one of the links.

7. The implantable device of claim 1, wherein the device closure pin includes a conical tip configured for insertion and lock-in into a receptacle.

8. The implantable device of claim 1, wherein the quick-release unit includes a release pin attaching the device closure pin to the quick-release unit, and wherein removal of the release pin releases the device closure pin from the quick-release unit.

9. The implantable device of claim 1, wherein a closed contour of the implantable device in the second rigid state is a three-dimensional curved shape including three arcs and two interconnecting sections where the two interconnecting sections are substantially straight.

10. The implantable device of claim 1, wherein each link has a hole and one of the pins, and wherein in each adjacent pair of the links, the pin of one of the links extends through the hole of the other one of the links.

11. An implantable device comprising:
    a multiplicity of links forming three arcs constructing a closed three-dimensional curved shape wherein for a plurality of the links, each link is connected to two other links;
    a device closure pin including a snap-in segment; and
    a lock-in unit attached and located at one end of the three arcs;
    a quick-release unit attached and located at an opposite end of the three arcs; and
    wherein the implantable device is flexible when the device closure pin is attached to one of the lock-in unit and the quick-release unit and is rigid when both sides of the device closure pin are attached to the lock-in unit and the quick-release unit; and
    wherein the lock-in unit includes a receptacle configured to receive and hold the snap-in segment of the device closure pin, wherein the receptacle of the lock-in unit is structured as a slotted spring washer configured to receive and hold the snap-in segment of the device closure pin.

12. The implantable device of claim 11, wherein the device closure pin includes at least one quick-release pinhole and wherein the quick-release unit includes a release pin attaching the device closure pin to the quick-release unit.

13. The implantable device of claim 11, wherein the closed three-dimensional curved shape of the implantable device is sufficiently large to prevent the implantable device from passing a pylorus.

14. A method of using an implantable device, comprising:
providing an implantable device including at least three arcs, a device closure pin, a lock-in unit attached and located at one end of the at least three arcs, and a quick-release unit attached and located at an opposite end of the at least three arcs; and
pulling a cord connected to the device closure pin to move the at least three arcs, the lock-in unit and the quick-release unit into a closed rigid configuration, which is a three-dimensional curved shape; and
wherein the implantable device with the three-dimensional curved shape comprises the at least three arcs and two interconnecting sections with each interconnecting section connecting the at least three arcs.

15. The method of claim 14 further comprising attaching the device closure pin to both the lock-in unit and the quick-release unit and holding the implantable device in a rigid state.

16. The method of claim 15, wherein the attaching of the device closure pin to the lock-in unit comprises pulling the cord to move a snap-in segment of the device closure pin into a locking mechanism of the lock-in unit.

17. The method of claim 14, wherein the at least three arcs comprise a plurality of links and where all link surfaces are atraumatic surfaces made of titanium, and wherein the atraumatic surfaces of the links further include a polytetrafluoroethylene coating or overcoat.

18. The method of claim 14, wherein the implantable device is in a flexible state when the device closure pin is coupled to one of the lock-in unit and the quick-release unit and is in a rigid state when the device closure pin is attached to both the lock-in unit and the quick-release unit.

* * * * *